(12) United States Patent
Eguchi

(10) Patent No.: US 8,866,096 B2
(45) Date of Patent: Oct. 21, 2014

(54) RADIOGRAPHIC IMAGE PHOTOGRAPHING SYSTEM AND CONTROL DEVICE

(75) Inventor: Yoshihiko Eguchi, Tokorozawa (JP)

(73) Assignee: Konica Minolta Medical & Graphic, Inc., Tokyo (JP)

(*) Notice: Subject to any disclaimer, the term of this patent is extended or adjusted under 35 U.S.C. 154(b) by 0 days.

(21) Appl. No.: 13/557,977

(22) Filed: Jul. 25, 2012

(65) Prior Publication Data

US 2012/0286167 A1 Nov. 15, 2012

Related U.S. Application Data

(62) Division of application No. 12/529,818, filed as application No. PCT/JP2008/052420 on Feb. 14, 2008, now abandoned.

(30) Foreign Application Priority Data

Mar. 14, 2007 (JP) ................. 2007-064704

(51) Int. Cl.
*G01T 1/24* (2006.01)
*A61B 6/00* (2006.01)

(52) U.S. Cl.
CPC ... *A61B 6/00* (2013.01); *G01T 1/24* (2013.01); *A61B 6/4233* (2013.01); *A61B 6/4494* (2013.01)
USPC ............. 250/370.09; 250/370.08; 250/370.11

(58) Field of Classification Search
CPC .................................... G01T 1/24; H05G 1/08
USPC .............................. 250/361 R, 370.08, 370.09
See application file for complete search history.

(56) References Cited

U.S. PATENT DOCUMENTS

| 7,737,427 B2* | 6/2010 | Kito et al. ...................... 250/580 |
| 2002/0079362 A1 | 6/2002 | Tsuchino |
| 2004/0079889 A1* | 4/2004 | Funabashi ................ 250/370.01 |
| 2005/0063512 A1* | 3/2005 | Maschke ......................... 378/91 |
| 2005/0104773 A1* | 5/2005 | Clarke et al. ............. 342/357.09 |

(Continued)

FOREIGN PATENT DOCUMENTS

| JP | 2004-141240 A | 5/2004 |
| JP | 2005-342305 A | 12/2005 |

(Continued)

OTHER PUBLICATIONS

English Language International Search Report dated Mar. 11, 2008 issued in parent International Application No. PCT/JP2008/052420.

(Continued)

*Primary Examiner* — Casey Bryant
(74) *Attorney, Agent, or Firm* — Holtz, Holtz, Goodman & Chick PC

(57) ABSTRACT

A radiographic image photographing system and its control device surely correlates radiographing order information with radiographic image data and facilitates radiographing work. A control section of a tag reader reads out inherent information stored in a tag in a radiation image detecting device. A control section of a radiographing operation apparatus receives the inherent information of the radiation image detecting device from the tag and stores it in a storing section. In response to an input from an input operation section, the control section correlates each piece of radiographing order information with a cassette ID of the radiation image detecting device and stores this correlation information in the storing section.

2 Claims, 12 Drawing Sheets

(56) References Cited

U.S. PATENT DOCUMENTS

| | | |
|---|---|---|
| 2006/0016998 A1* | 1/2006 | Ohara .................... 250/370.11 |
| 2006/0182324 A1* | 8/2006 | Motoki ....................... 382/128 |
| 2006/0186342 A1 | 8/2006 | Burger et al. |
| 2007/0269017 A1 | 11/2007 | Umeki et al. |
| 2009/0022276 A1 | 1/2009 | Ohara |
| 2009/0103796 A1 | 4/2009 | Akagi et al. |
| 2009/0196398 A1 | 8/2009 | Ohara |

FOREIGN PATENT DOCUMENTS

| | | |
|---|---|---|
| JP | 2006-026283 A | 2/2006 |
| JP | 2006-122304 A | 5/2006 |
| JP | 2006-223465 A | 8/2006 |
| WO | WO 2006/095538 A1 | 9/2006 |
| WO | WO 2006/109551 A1 | 10/2006 |
| WO | WO 2006/129498 A1 | 12/2006 |

OTHER PUBLICATIONS

Japanese Office Action dated Jul. 9, 2013 (and English translation thereof) in counterpart Japanese Application No. 2013-067751.

Japanese Office Action dated Nov. 11, 2013 (and English translation thereof) issued in counterpart Japanese Application No. 2013-067751.

* cited by examiner

FIG. 2

| RADIOGRAPHING ORDER ID (P1) | PATIENT ID (P2) | PATIENT NAME (P3) | SEX (P4) | AGE (P5) | DEPARTMENT (P6) | RADIOGRAPHING BODY PART (P7) | RADIOGRAPHING DIRECTION (P8) |
|---|---|---|---|---|---|---|---|
| 001 | 100085 | ICHIRO SUZUKI | MALE | 25 | SURGERY | CHEST | LATERAL L |
| 002 | 100085 | ICHIRO SUZUKI | MALE | 25 | SURGERY | CHEST | LATERAL R |
| 003 | 100085 | ICHIRO SUZUKI | MALE | 25 | SURGERY | LEG | L |
| 004 | 100085 | ICHIRO SUZUKI | MALE | 25 | SURGERY | LEG | R |
| 005 | 100125 | RIN YAGUCHI | FEMALE | 55 | GYNECOLOGY | BREAST | MLO-R |
| 006 | 100125 | RIN YAGUCHI | FEMALE | 55 | GYNECOLOGY | BREAST | MLO-L |
| 007 | 100125 | RIN YAGUCHI | FEMALE | 55 | GYNECOLOGY | BREAST | CC-L |
| 008 | 100125 | RIN YAGUCHI | FEMALE | 55 | GYNECOLOGY | BREAST | CC-R |
| 009 | 100320 | JIRO SATO | MALE | 15 | ORTHOPEDICS | LEG | L |
| 010 | 100325 | EISAKU YOSHIDA | MALE | 60 | ORTHOPEDICS | HAND | L |

FIG. 7

PLEASE INPUT RADIOGRAPHING ORDER INFORMATION FOR THE SCHEDULED RADIOGRAPHING

| RADIOGRAPHING ORDER ID | PATIENT ID | PATIENT NAME | SEX | AGE | DEPARTMENT | RADIOGRAPHING BODY PART | RADIOGRAPHING DIRECTION |
|---|---|---|---|---|---|---|---|
| 001 | 100085 | ICHIRO SUZUKI | MALE | 25 | SURGERY | CHEST | LATERAL L |
| 002 | 100085 | ICHIRO SUZUKI | MALE | 25 | SURGERY | CHEST | LATERAL R |
| 003 | 100085 | ICHIRO SUZUKI | MALE | 25 | SURGERY | LEG | L |
| 004 | 100085 | ICHIRO SUZUKI | MALE | 25 | SURGERY | LEG | R |
| 005 | 100125 | RIN YAGUCHI | FEMALE | 55 | GYNECOLOGY | BREAST | MLO-R |
| 006 | 100125 | RIN YAGUCHI | FEMALE | 55 | GYNECOLOGY | BREAST | MLO-L |
| 007 | 100125 | RIN YAGUCHI | FEMALE | 55 | GYNECOLOGY | BREAST | CC-L |
| 008 | 100125 | RIN YAGUCHI | FEMALE | 55 | GYNECOLOGY | BREAST | CC-R |
| 009 | 100320 | JIRO SATO | MALE | 15 | ORTHOPEDICS | LEG | L |
| 010 | 100325 | EISAKU YOSHIDA | MALE | 60 | ORTHOPEDICS | HAND | L |

(DECIDE) (RETURN)

FIG. 8

| RADIOGRAPHING ORDER ID | PATIENT ID | PATIENT NAME | SEX | AGE | DEPARTMENT | RADIOGRAPHING BODY PART | RADIOGRAPHING DIRECTION |
|---|---|---|---|---|---|---|---|
| 001 | 100085 | ICHIRO SUZUKI | MALE | 25 | SURGERY | CHEST | LATERAL L |
| 002 | 100085 | ICHIRO SUZUKI | MALE | 25 | SURGERY | CHEST | LATERAL R |
| 003 | 100085 | ICHIRO SUZUKI | MALE | 25 | SURGERY | LEG | L |
| 004 | 100085 | ICHIRO SUZUKI | MALE | 25 | SURGERY | LEG | R |
| 009 | 100320 | JIRO SATO | MALE | 15 | ORTHOPEDICS | LEG | L |
| 010 | 100325 | EISAKU YOSHIDA | MALE | 60 | ORTHOPEDICS | HAND | L |

PLEASE INPUT RADIOGRAPHING ORDER INFORMATION FOR THE RADIOGRAPHING TO BE STARTED NOW (DECIDE)  (RETURN)

FIG. 9

PLEASE INPUT RADIATION IMAGE DETECTING DEVICE (FPD)

| RADIOGRAPHING ORDER ID | PATIENT ID | PATIENT NAME | SEX | AGE | DEPARTMENT | RADIOGRAPHING BODY PART | RADIOGRAPHING DIRECTION | FPD | |
|---|---|---|---|---|---|---|---|---|---|
| 001 | 100085 | ICHIRO SUZUKI | MALE | 25 | SURGERY | CHEST | LATERAL L | 10 | 20 |
| 002 | 100085 | ICHIRO SUZUKI | MALE | 25 | SURGERY | CHEST | LATERAL R | 10 | 20 |
| 003 | 100085 | ICHIRO SUZUKI | MALE | 25 | SURGERY | LEG | L | 10 | 20 |
| 004 | 100085 | ICHIRO SUZUKI | MALE | 25 | SURGERY | LEG | R | 10 | 20 | h21                                                                                    h23

| CASSETTE ID | TYPE OF SCINTILLATOR | SIZE | PIXEL SIZE |
|---|---|---|---|
| FPD10 | CsI | 14" x 17" | 100 μm |
| FPD20 | NaI | 14" x 14" | 200 μm | h22

(END RADIOGRAPHING)   (RETURN)   (DECIDE)
      h26              h25        h24

H2

RADIOGRAPHIC IMAGE PHOTOGRAPHING SYSTEM AND CONTROL DEVICE

This application is a Divisional Application of U.S. application Ser. No. 12/529,818, filed Sep. 3, 2009 now abandoned, which is a U.S. National Phase Application under 35 USC 371 of International Application No. PCT/JP2008/052420, filed Feb. 14, 2008, which further claims priority of Japanese Application No. 2007-064704, filed Mar. 14, 2007, the entire contents of all of which are incorporated herein by reference.

FIELD OF THE INVENTION

The present invention relates to a radiographic image photographing system for performing photographic operations using the radiation represented by X-rays, and a control device thereof.

BACKGROUND OF THE INVENTION

In the field of medical diagnosis, a CR (Computed Radiography) system capable of handling a radiographic image as digital data is put into practical use. This CR system employs a CR cassette incorporating a phosphor plate. A part of the applied radiation is stored into the phosphor plate as radiation energy, and the phosphor plate is scanned by excitation light to obtain radiographic image data.

In recent years, to meet the requirements of a medical institute provided with a plurality of radiographing rooms, a large-sized CR system is operating on a practical level. In this large-sized CR system, there are a plurality of patients to be radiographed at one time and a plurality of radiographing technicians to perform radiographing operations. This may cause confusion of radiographic image data among different patients. To solve this problem, the instruction which is named radiographing order information including the patient information (name and age of a patient) and radiographic information (date, region and direction of radiographing) is generated in advance. Then this radiographing order information is correlated with the cassette ID (identification information) for identifying the CR cassette and is stored in a control device.

In an FPD (Flat Panel Detector) apparatus having been developed (Patent Literature 1, for example) instead of the aforementioned CR cassette, a radiation detection element arranged on a substrate in a two-dimensional array is incorporated and the electric signal in response to the amount of radiation applied to the radiation detecting element is outputted. This FPD apparatus permits the radiographic image data to be obtained directly, and allows the system structure to be simplified as compared with the CR cassette, whereby smooth radiographing operation is ensured. Further, a plurality of pieces of radiographic image data can be stored by the storage section incorporated in the FPD apparatus, whereby continuous radiographing operations are enabled by one FPD apparatus and radiographing efficiency is enhanced.

In the radiographing operation using the FPD apparatus, in order to ensure that a desired image quality is obtained independently of different radiographing conditions such as the physical build of a patient and the region of radiographing, it is preferred to prepare a plurality of FPD apparatuses each having a different size and type of the scintillator, and to use these FPD apparatuses in conformance to the particular radiographing conditions (Patent Literature 2, for example). However, the FPD apparatus is very expensive. Especially when different FPD apparatuses are to be used in conformance to the particular radiographing conditions as mentioned above, it is important to configure a radiographic system wherein the utilization efficiency of the FPD apparatuses is enhanced. Thus, in a large-scale medical facility provided with a plurality of radiographing rooms wherein a plurality of radiographing technicians are assigned to perform radiographing work, it is assumed to configure an arrangement wherein a plurality of FPD apparatuses are collectively stored in a storage site outside the radiographing room, and the plurality of FPD apparatuses are used by a plurality of radiographing technician.

In this arrangement, a radiographing technician specifies radiographing order information by means of a control device, and selects one FPD apparatus conforming to the radiographing order information for scheduled radiographing, from among a plurality of FPD apparatuses, and the radiographing order information for scheduled radiographing is sent to the selected FPD apparatus. After that, the selected FPD apparatus is taken out of the common storage site, and radiographing operation is performed according to the radiographing order information using the selected FPD apparatus.

However, the FPD apparatuses are similar to one another in appearance. Thus, an FPD apparatus different from the one having been selected may be taken out of the common storage site, with the result that the radiographic image data having been generated cannot be correlated with the radiographing order information. This may require the radiographing operation to be repeated. It is possible to configure a structure wherein the FPD apparatus is equipped with a light emitting section or display section, and selection of that particular FPD apparatus is notified by the light emitting section or display section of the selected FPD apparatus, whereby incorrect use of the FPD apparatus can be prevented. This structure, however, may increase the size of the FPD apparatus and production costs.

In one of the techniques having been disclosed (Patent Literature 3), the inlet of a radiographing room is equipped with a sensor for detecting the FPD apparatus. When the sensor has detected that the FPD apparatus is taken out of the storage site and is brought into the radiographing room, the radiographing order information for scheduled radiographing selected in advance is sent to the FPD apparatus. According to this technique, the radiographing order information is sent to the FPD apparatus that is brought into the radiographing room and is used for the radiographing. The radiographic image data is generated by this FPD apparatus. This arrangement ensures precise correlation between the radiographic image data and radiographing order information.

Patent Literature 1: Japanese Unexamined Patent Application Publication No. 2006-122304
Patent Literature 2: Japanese Unexamined Patent Application Publication No. 2006-26283
Patent Literature 3: Japanese Unexamined Patent Application Publication No. 2004-141240

SUMMARY OF THE INVENTION

Problems to be Solved by the Invention

In Patent Literature 3, however, the selected radiographing order information is automatically sent to an FPD apparatus brought into the radiographing room. For example, assuming that a plurality of radiographing technicians have each sent the radiographing order information to the control device of one radiographing room for the purpose of using the same radiographing room. In this case, if the order in which the FPD apparatuses each carried by each radiographing technician reach the radiographing room is different from the order of the radiographing order information sent by each radiographing technician, then the radiographing order information different from the desired radiographing order information will be sent to the FPD apparatus. This will cause incorrect capturing of radiographic image data.

In some mode of radiographing, a plurality of FPD apparatuses having different types of scintillators may have to be used to radiograph one patient. However, the structure disclosed in the aforementioned Patent Literature 3 fails to meet the requirements of this method of radiographing.

When the FPD apparatus has entered the radiographing room, the radiographing order information is sent to the FPD apparatus. Thus, when radiographing order information is to be sent additionally to this FPD apparatus, the FPD apparatus has to be taken out once of the radiographing room and has to be put into the radiographing room again. Thus, when radiographing of one patient is immediately followed by the radiographing of another patient, in order that the radiographing order information of the other patient is sent to the FPD apparatus, the FPD apparatus must be once brought out of the radiographing room. This procedure greatly disturbs the radiographing work.

In view of these problems described above, it is an object of the present invention to provide a radiographic image photographing system which, when a FPD apparatus is used as a radiation image detecting device, ensures precise correlation between the radiographing order information and radiographic image data and provides smooth radiographing work, and to provide a control device for this radiographic image photographing system.

Means for Solving the Problems

To achieve the aforementioned object, the radiographic image photographing system of the present invention performs radiographing operations based on the radiographing order information for radiographing, and includes:

at least one portable radiation image detecting device provided with an image data generation section that detects the radiation having passed through a subject and generates the radiographic image data in conformance to the amount of the radiation; and an RFID tag for storing inherent information; and an RFID tag reader for reading the inherent information stored in the RFID tag, when the radiation image detecting device has entered a predetermined area of the radiographing room where radiographing operations are performed;

a control device including:

an acquisition section for acquiring the aforementioned radiographing order information and the inherent information read by the RFID tag reader;

a storing section for storing the radiographing order information and the inherent information acquired by the acquisition section;

a display section for displaying the radiographing order information and the inherent information stored in the storing section;

an inherent information selection device for selecting one piece of inherent information from among the inherent information displayed on the display section; and a correlation device for establishing correlation between one piece of inherent information selected by the inherent information selection device and the aforementioned radiographing order information.

The control device of the present invention for achieving the aforementioned object is a control device connected with an RFID tag reader for reading the RFID tag provided in the radiation image detecting device when at least one of the radiation image detecting devices has entered a predetermined area of the radiographing room wherein this radiation image detecting device detects the radiation having passed through a subject and generates the radiographic image data. This control device includes:

an acquisition section for acquiring the radiographing order information for radiographing operation and the inherent information of the radiation image detecting device read by the RFID tag reader;

a storing section for storing the radiographing order information and the inherent information acquired by the acquisition section;

a display section for displaying the radiographing order information and the inherent information stored in the storing section;

an inherent information selection device for selecting one piece of inherent information from among the inherent information displayed on the display section; and a correlation device for establishing correlation between one piece of inherent information selected by the inherent information selection device and the aforementioned radiographing order information.

Effects of the Invention

According to the present invention, the inherent information stored in the tag of the radiation image detecting device is read by the tag reader and the inherent information is displayed by the control device. The radiation image detecting device of the desired inherent information is selected, and the radiation image detecting device of the desired inherent information having been selected is correlated with the radiographing order information. Thus, even when a plurality of radiographing technicians are to perform radiographing operations in the same radiographing room using radiation image detecting devices, correct correlation is ensured between radiographing order information for scheduled radiographing and the radiation image detecting device for their own use.

The correlation for a plurality of pieces of radiographing order information can be established at one time. Accordingly, even when a plurality of radiographing operations are performed for one patient as in the case of photographing both the front and side of the chest, efficiency is enhanced in the operation flow of the radiographing technician.

BRIEF DESCRIPTION OF THE DRAWINGS

FIG. 2 is a diagram representing an example of a radiographing order information list.

FIG. 7 is an example wherein the input screen for inputting the radiographing order information for scheduled radiographing is displayed on a display section.

FIG. 8 is an example wherein the input screen for inputting the radiographing order information for radiographing to be started now is displayed on the display section 17.

FIG. 9 is an example wherein the input screen for inputting selection of the radiation image detecting device is displayed on the display section 17.

DESCRIPTION OF REFERENCE NUMERALS

Figure 1:
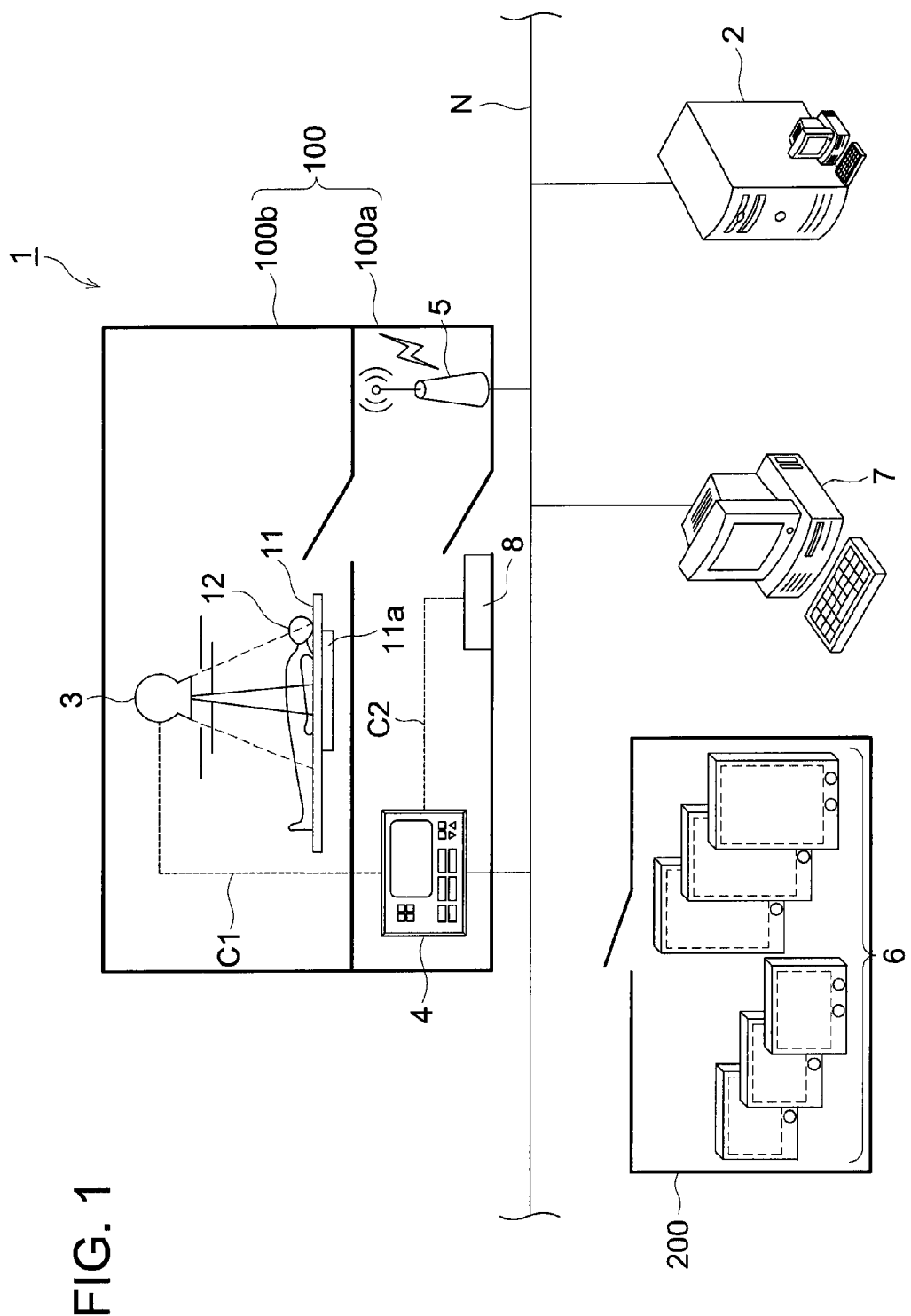
FIG. 1 is a diagram representing the overall structure of an embodiment of a radiographic image photographing system.

1. Radiographic image photographing system
4. Radiographing operation apparatus
6. Radiation image detecting device
7. Console
8. Tag reader
14. Control section
15. RAM
16. ROM
17. Display section
18. Input operation section
19. Communication section
21. Storing section
62. Imaging panel
66. Storing section
68. Tag
100. Radiographing room
200. Storage room

BEST MODE FOR CARRYING OUT THE PRESENT INVENTION

The following describes the embodiment of the present invention with reference to the drawings. It should be noted that the technical scope of the present invention is not restricted by the description of the present embodiment.

FIG. 1 is a diagram representing the overall structure of an embodiment of the radiographic image photographing system 1 in the present invention.

As shown in FIG. 1, the radiographic image photographing system 1 of the present embodiment includes a management server 2 for managing the information on radiographing, a radiographing operation apparatus 4 for performing an operation relating to radiographing, a base station 5 for performing wireless communication, for example, via the wireless LAN (Local Area Network) and a console 7 for applying image processing to the radiographic image data generated by the radiation image detecting device 6, wherein these components are connected via the network.

Although not illustrated, the radiographic image photographing system 1 is connected via the network N with the HIS (Hospital Information System) or RIS (Radiology information system) for centralizing management of the patient diagnostic information and accounting information. The network N can be the communication circuit dedicated to this system. However, an existing line such as the Ethernet (registered trademark) is preferably used since otherwise the degree of freedom in the system configuration is reduced.

The radiographing room 100 includes a radiographing room 100b shielded by lead and a front room 100a arranged on the front thereof. The radiographing operation apparatus 4, the base station 5 and the tag reader 8 for detecting a tag incorporated in the radiation image detecting device 6 are arranged in the front room 100a, while the radiographing apparatus 3 for applying radiation to a subject is arranged in the radiographing room 100b. The radiographing operation apparatus 4 is connected with the radiographing apparatus 3 through a cable C1, and with the tag reader 8 through a cable C2.

Although not illustrated, a plurality of radiographing rooms 100 can be connected in conformity to the scale and configuration of the facility. Thus, a plurality of radiographing operations can be performed by one radiation image detecting device 6 in a plurality of radiographing rooms 100.

The storing room 200 provides a space for collective storage of a plurality of radiation image detecting devices 6 with different types of scintillators and sizes. This storing room 200 is located outside the radiographing room 100 so that the radiation image detecting device 6 stored therein can be used jointly by a plurality of radiographing technicians.

The following describes the structure of the devices.

The management server 2 includes a computer, and is provided with a control section for controlling various sections constituting the management server 2, an input operation section for inputting various forms of information and user instructions, and an external storage device for storing various forms of information (not illustrated). The control section generates the radiographing order information by correlating the patient information with the radiographic information, which are inputted from the input operation section and ensures that a plurality of pieces of radiographing order information are stored in the external storage device in the form of a radiographing order information list.

FIG. 2 is a diagram representing an example of the radiographing order information list made up of a plurality of pieces of radiographing order information. As shown in FIG. 2, radiographing order information includes the patient information such as patient ID P2, patient name P3, sex P4 and age P5; and the radiographic information such as department P6, radiographing body part P7 and radiographing direction P8. According to the sequence of receiving the order, radiographing order information is automatically assigned with radiographing order ID P1. Without being restricted to the aforementioned examples, the patient information and radiographic information can include the information on patient birth date, number of times of examination and dose of radiation. Alternatively, there is no need to include all of such information. The information contained in the radiographing order information can be set in conformity to the purpose of radiographing and the flow of radiographing.

The radiographing apparatus 3 applies radiation to the patient 12 lying on the recumbent position radiographic stand 11. A detecting device mounting port 11a for mounting the radiation image detecting device 6 is provided below the recumbent position radiographic stand 11. The radiographing apparatus 3 is controlled by the radiographing operation apparatus 4 and performs radiographing operation under a predetermined condition.

The base station 5 has a function of relaying wireless communication when communicating between the radiation image detecting device 6 and console 7. Wireless communication includes the light wireless communication using the infrared rays and visible rays (laser and others), as well as acoustic communication using a sound wave or ultrasonic wave in addition to radio wave (space wave).

The console 7 includes a computer, and is provided with a control section for controlling various sections constituting the console 7, a display section for displaying the radiographing order information list sent from the management server 2, an input operation section for inputting radiographing order information for scheduled radiographing, and an external storage device for storing radiographic image data sent from the radiation image detecting device 6 (none of them are illustrated).

The control section receives the radiographing order information list from the management server 2 and displays the radiographing order information list on the display section. Further, the control section receives inputs from the input operation section and sends the selected radiographing order information to the radiographing operation apparatus 4 in the radiographing room to be immediately used. The control section applies predetermined image processing to the radiographic image data sent by wireless communication from the radiation image detecting device 6 through the base station 5, and establishes correlation between the radiographic image data and radiographing order information, which are stored in the external storage device. When a plurality of consoles 7 are connected to the network N, communication can be made by attaching the console ID to ensure that the image will go back to the console 7 having selected the radiographing order information.

The tag reader 8 is located in the vicinity of the front room 100a of the radiographing room 100, and uses the RFID (Radio Frequency Identification) technique to exchange information with the radiation image detecting device 6 brought into the front room 100a. To put it more specifically, in the tag reader 8, predetermined instruction information is included in the electromagnetic field and radio wave via the built-in antenna and is transmitted. The radiation image detecting device 6 having entered the predetermined range of the radiographing room 100 is detected. Then the tag reader 8 reads the inherent information stored by the tag (RFID tag) of the radiation image detecting device 6. The inherent information having been read is sent to the radiographing operation apparatus 4 through the cable C2.

(Radiographing Operation Apparatus)

Figure 3:
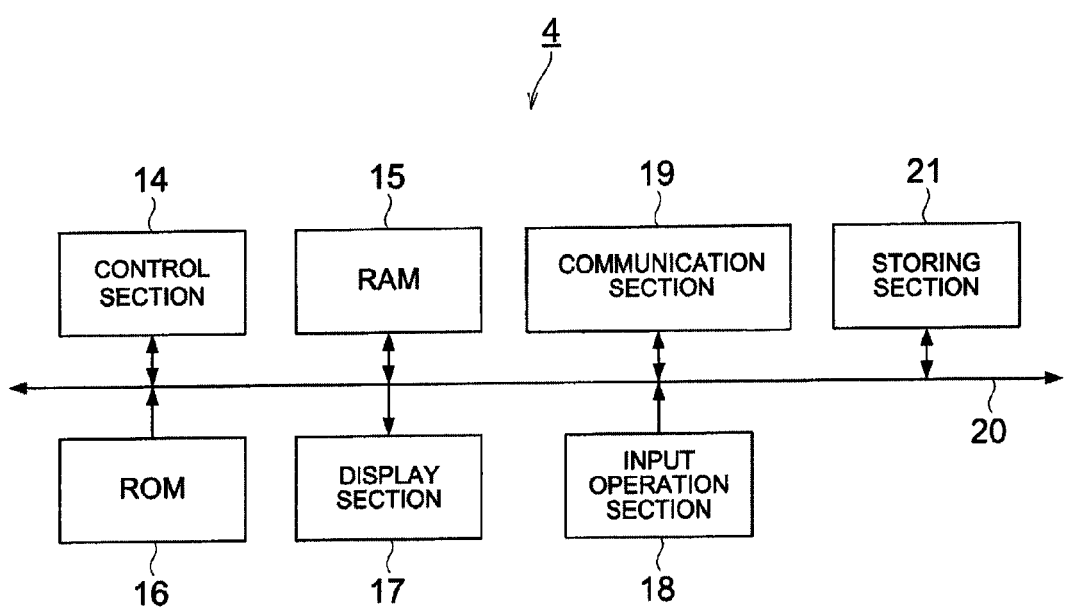
FIG. 3 is a block diagram representing the major structure of a radiographing operation apparatus.

FIG. 3 is a block diagram representing the major structure of the radiographing operation apparatus 4. As shown in FIG. 3, the radiographing operation apparatus 4 as a control device is made up of a computer including a control section 14, RAM 15, ROM 16, display section 17, input operation section 18, communication section 19 and storing section 21. These components are connected via the bus 20.

The ROM (Read Only Memory) 16 is made of a nonvolatile semiconductor memory and stores the control program executed by the control section 14, and image processing conditions.

The RAM (Random Access Memory) 15 forms a work area for temporarily storing the programs which are read from the ROM 16 and can be executed by the control section 14, input or output data, and parameters in various steps of processing executed and controlled by the control section 14.

The display section 17 includes a CRT (Cathode Ray Tube) and LCD (Liquid Crystal Display), and displays various screens in conformity to the instruction of the inputted display signal outputted from the control section 14. For example, the display section 17 displays a plurality of radiographing order information received through the communication section 19 and the inherent information of the radiation image detecting device 6 (to be described later).

The input operation section 18 is made up of a keyboard or mouse, for example, and the key depression signal produced by depressing the key on the keyboard or operation signal produced by the mouse is outputted to the control section 14 as the input signal. To put it more specifically, the input operation section 18 can be used to input the radiographing order information for scheduled radiographing, selected from among a plurality of pieces of radiographing order information displayed on the display section 17. Further, the input operation section 18 can be used to input selection of the radiation image detecting device 6 to be used for radiographing order information for scheduled radiographing.

The communication section 19, as an acquisition section and transmission section, provides an interface for communication with other devices. The communication section 19 can be used for various forms of communication with the console 7 via the network N, with the radiographing apparatus 3 through the cable C1, and with the tag reader 8 through the cable C2. Further, the communication section 19 can be used for wireless communication with the radiation image detecting device 6 located inside the front room 100a by short-distance wireless communication such as the wireless PAN (Personal Area Network) based on the techniques of Bluetooth and IrDA.

The control section 14 is made up of the CPU (Central Processing Unit), for example. The control section 14 reads a predetermined program stored in the ROM 16, and expands it in the work area of the RAM 15. Then various forms of processing are performed according to this program. Based on the information inputted from the input operation section 18, the control section 14 selects the radiographing order information for scheduled radiographing by one radiographing technician, out of a plurality of pieces of radiographing order information having been sent from the console in advance. The control section 14 also selects the radiation image detecting device 6 to be used for the radiographing order information for scheduled radiographing. Further, the control section 14 establishes a correlation between the radiographing order information for scheduled radiographing and the radiation image detecting device 6 to be used for radiographing, to be stored in the storing section 21. To put it another way, the control section 14 corresponds to the order selection device, inherent information selection device and correlation device in the present invention.

The storing section 21 stores the inherent information of the radiation image detecting device 6 received from the tag reader 8 through the communication section 19 and the radiographing order information received from the console 7. The storing section 21 also stores the correlation information representing the correlation established by control section 14 between the radiographing order information and the radiation image detecting device 6.

(Radiation Image Detecting Device)

The radiation image detecting device 6 is kept in the storing room 200 located outside the radiographing room 100, and the radiation image detecting devices 6 of different types of scintillators and sizes are collectively kept in the storing room 200. The radiation image detecting device 6 detects the radiation applied from the radiographing apparatus 3 and having passed through the patient 12, whereby the radiographic image data is acquired. It is a portable cassette FPD apparatus composed of an imaging panel called Flat Panel Detector (FPD) stored in a cassette.

Figure 4:
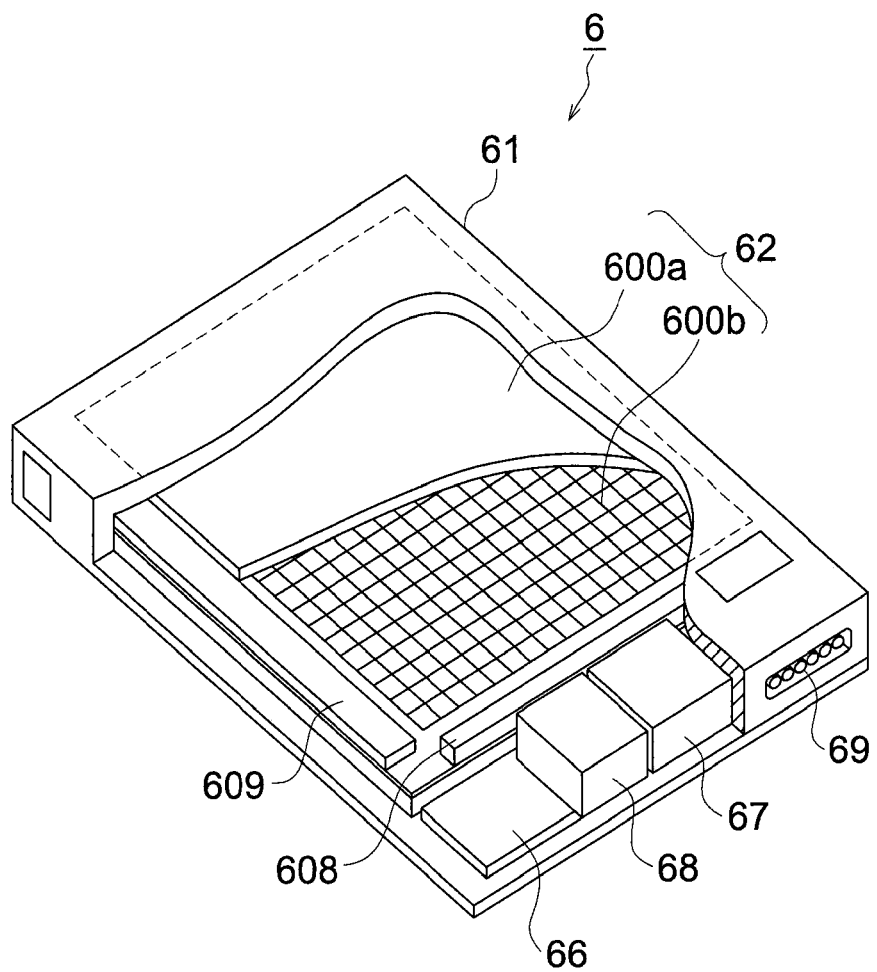
FIG. 4 is a perspective view representing a radiation image detecting device.
Figure 5:
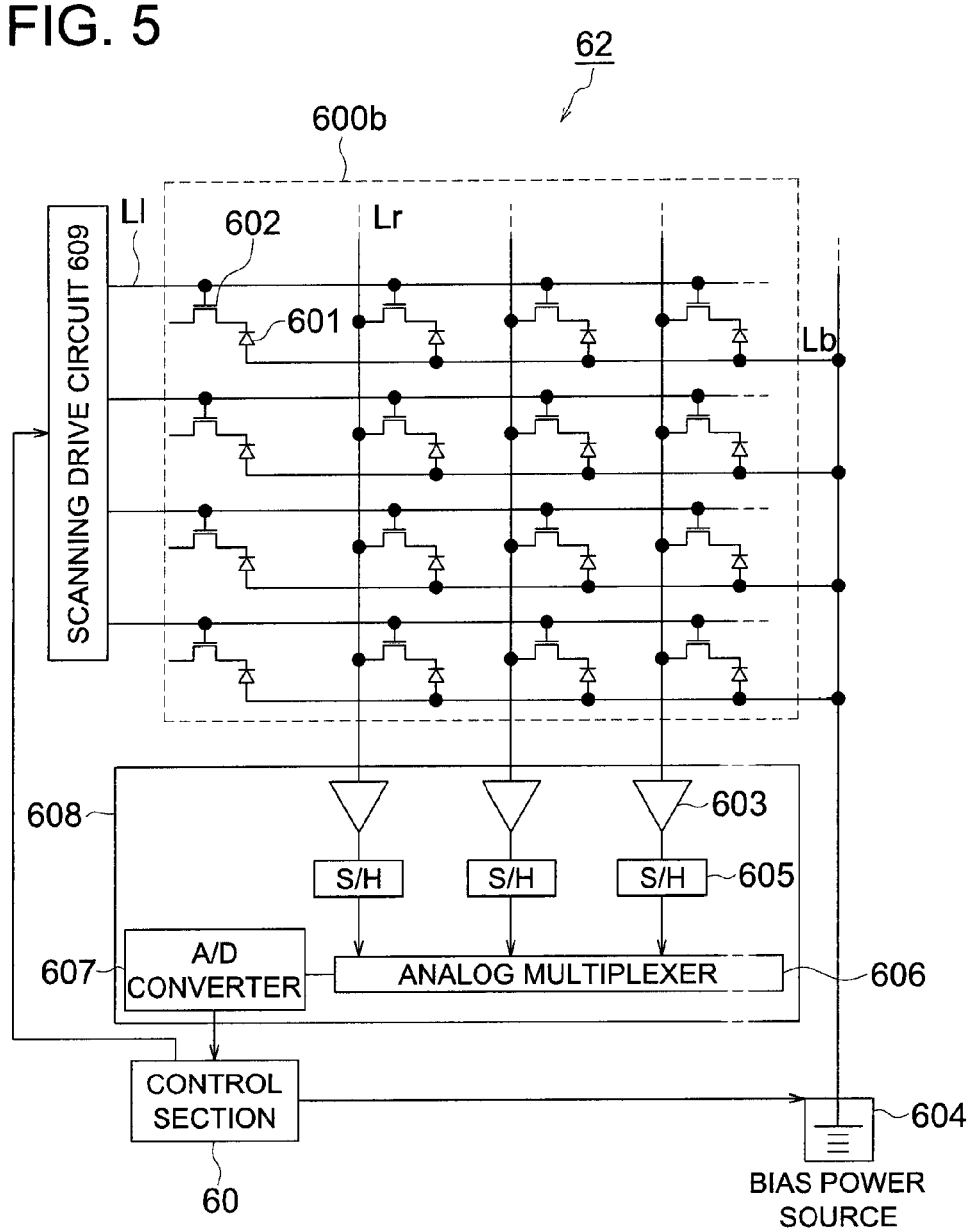
FIG. 5 is an equivalent circuit diagram of the signal detecting section wherein photoelectric conversion sections are arranged in a two-dimensional array.

The following describes the structure of the radiation image detecting device 6 by referring to FIGS. 4 and 5. FIG. 4 is a perspective view representing the radiation image detecting device 6. As shown in FIG. 4, the radiation image detecting device 6 is provided with a casing 61 for protecting the interior, and is designed in a cassette structure to enhance portability.

The casing 61 incorporates the imaging panels 62 which are formed in layers as image data generating sections for converting the applied radiation into electric signals. A light emitting layer 600a for emitting light in response to the intensity of the radiation being applied is provided on the side of the imaging panel 62 to be exposed to the radiation.

The light emitting layer 600a is called a scintillator layer (or scintillator) simply, and is made of a phosphor as the major component, for example. Based on the incident light, the light emitting layer 600a outputs an electromagnetic wave having a wavelength of 300 nm through 800 nm, namely, an electromagnetic wave (light) ranging from the ultraviolet light to the infrared light centering on the visible light.

A signal detecting section 600b composed of photoelectric conversion sections arranged in a matrix is formed on the side of the light emitting layer 600a opposite to the side exposed to the radiation. These photoelectric conversion sections convert the electromagnetic wave (light) emitted from the light emitting layer 600a, into electric energy, and stores this electric energy, and then outputs the image signal based on the stored electric energy. The signal outputted from one of the photoelectric conversion sections corresponds to one pixel as the minimum unit constituting the radiographic image data.

The following describes the circuit structure of the imaging panel 62. FIG. 5 is an equivalent circuit diagram of the signal detecting section 600b in which photoelectric conversion sections are arranged in a two-dimensional array. As shown in FIG. 5, the photoelectric conversion section includes a photo diode 601, and a thin film transistor (TFT) 602 for capturing the electric signal obtained by switching the electric energy stored in the photo diode 601.

The electric signal having been captured is amplified by an amplifier 603 to the level that can be detected by a signal reading circuit 608. The amplifier 603 is connected with a reset circuit (not illustrated) made up of a TFT 602 and a capacitor. Switching of the TFT 602 allows resetting operations to be performed, whereby the stored electric signal is reset.

A scanning line Ll and signal line Lr are arranged between photoelectric conversion sections so as to cross each other. One end of the aforementioned photo diode 601 is connected with the TFT 602 and is further connected with the signal line Lr through this TFT 602. In the meantime, the other end of the photo diode 601 is connected with one end of the adjacent photo diode 601 arranged in each row and is connected with the bias power source 604 through the common bias line Lb. One end of this bias power source 604 is connected with the control section 60. Voltage is applied to the photo diode 601 through the bias line Lb according to the instruction from the control section 60.

The gate of the TFT 602 arranged in each row is connected with the common scanning line Ll. The scanning line Ll is connected with the control section 60 through the scanning drive circuit 609 for sending pulses to each photoelectric conversion section. Similarly, one end of the photo diode 601 arranged in each column is connected with the common signal line Lr, and is further connected with the signal reading circuit 608 that is controlled by the control section 60. In the signal reading circuit 608, an amplifier 603, sample hold circuit 605, analog multiplexer 606 and A/D converter 607 are arranged on the common signal line Lr in the order closer to the imaging panel 62.

When signals are read, the scanning drive circuit 609 drives the TFT 602 to pass current, whereby the charge stored in the photo diode 601 is sent to the amplifier 603 as an electric signal. This electric signal is amplified by the amplifier 603 to the level that can be read by the signal reading circuit 608. The voltage of the amplifier 603 is temporarily held by the sample hold circuit 605 and is then sent to the analog multiplexer 606.

The analog multiplexer 606 converts the voltage having been obtained into a serial electric signal, and sends it to the A/D converter 607, which converts the electric signal to digital data. In this manner, radiographic image data is generated by the imaging panel 62.

Going back to FIG. 4, the radiation image detecting device 6 is also provided with a storing section 66, power source section 67 and charging terminal 69.

The storing section 66 is made of a rewritable memory such as nonvolatile memory or flash memory, and is capable of storing the radiographic image data on the order of several sheets through several tens of sheets outputted from the imaging panel 62. This storing section 66 can be a built-in memory, or a detachable memory such as a memory card.

The power source section 67 supplies power to a plurality of drive sections (control section 60, imaging panel 62, storing section 66 and others) constituting the radiation image detecting device 6.

The tag 68 is a so-called RFID tag, and includes a control circuit for controlling various parts of the tag 68, a storing section for storing the inherent information of the radiation image detecting device 6, and an antenna for transmitting and receiving an electromagnetic field and radio wave (not illustrated). The tag 68 is designed to ensure that, when the electromagnetic field and radio wave transmitted from the tag reader 8 has been received through the antenna, the inherent information stored in the storing section is sent to the tag reader 8 through the antenna. The inherent information is exemplified by the cassette ID as the inherent identification information assigned to each of the radiation image detecting devices 6. In addition, scintillator type information, size information and resolution can be included. The size information includes the information on the size that can be radiographed, as exemplified by an 8×10-inch size or 14×17-inch size. It also includes information on the size of the radiation image detecting device 6.

Figure 6:
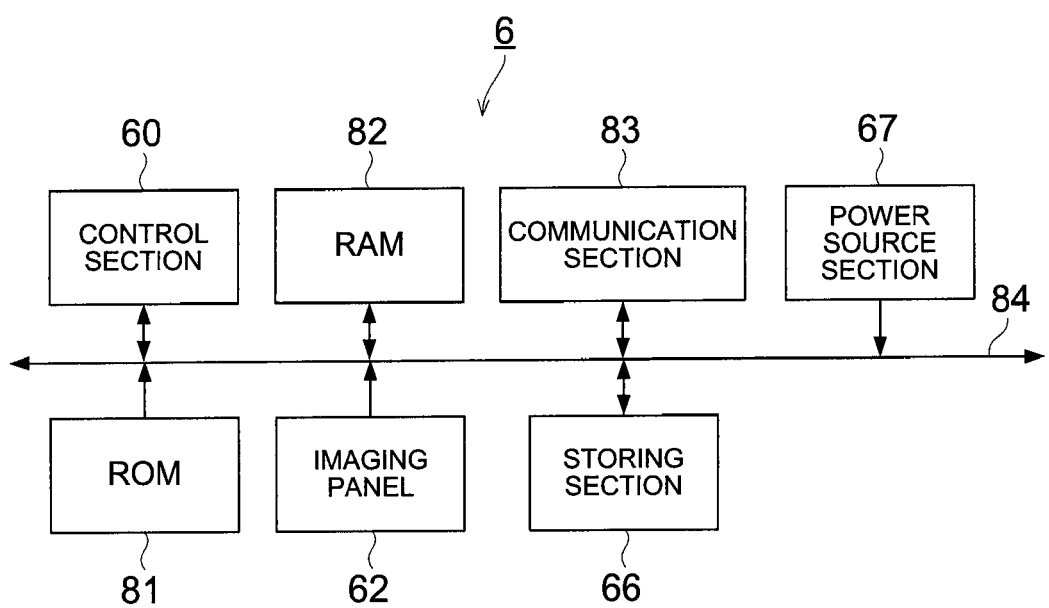
FIG. 6 is a block diagram representing the major structure of the radiation image detecting device.

FIG. 6 is a block diagram representing the major structure of the radiation image detecting device 6. As shown in FIG. 6, the control system of the radiation image detecting device 6 is provided with a control section 60, imaging panel 62, storing section 66, power source section 67, ROM 81, RAM 82 and communication section 83. These components are connected by the bus 84. Of these components, the imaging panel 62, storing section 66 and power source section 67 have already been mentioned, and will not be described to avoid duplication.

The ROM 81 is made of a nonvolatile semiconductor memory and others, and is used to store the control program to be executed by the control section 60.

The RAM 82 forms a work area for temporarily storing various types of programs which are read from the ROM 81 and can be executed by the control section 60, input or output data, and parameters in various forms of processing executed by the control section 60.

The communication section 83 provides wireless communication to exchange various forms of information with the console 7 through a base station 5 by the wireless LAN conforming to the 802.11 Standards of IEEE (Institute of Electrical and Electronic Engineers). Further, the communication section 83 provides wireless communication with the radiographing operation apparatus 4 in the front room 100a by short-distance wireless communication such as wireless PAN.

The control section 60 is made up of a CPU and others, for example. The control section 60 reads out the control program stored in the ROM 81, and expands it in the work area formed inside the RAM 82. Various sections of the radiation image detecting device 6 are controlled according to this control program. For example, through collaboration with the communication section 83, the control section 60 receives radiographing order information from the radiographing operation apparatus 4, and sends this radiographing order information and radiographic image data to the console 7 through the base station 5.

Figure 10:
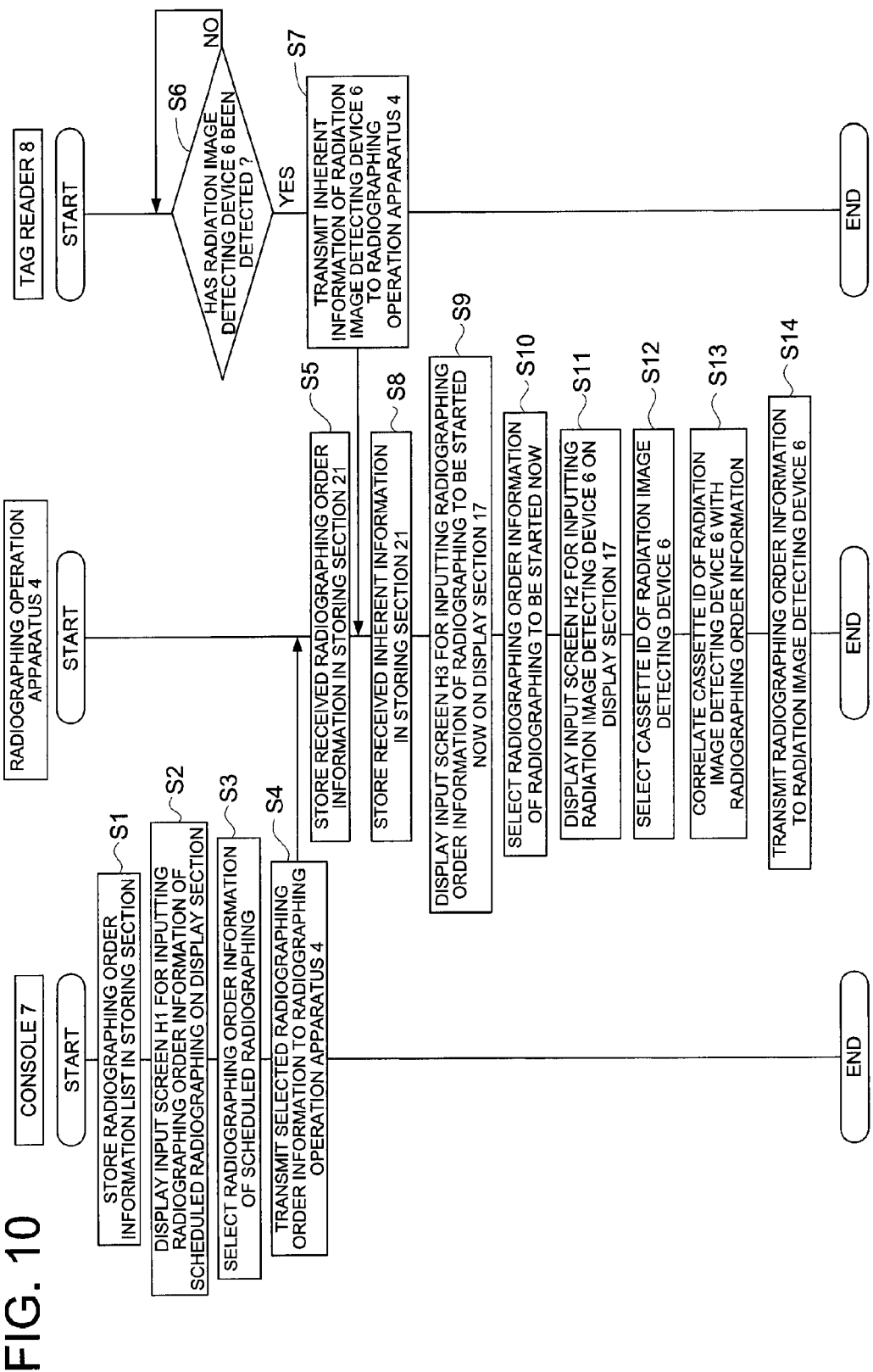
FIG. 10 is a flow chart representing the operations of the radiographic image photographing system.

FIG. 10 is a flow chart representing the operations of the radiographic image photographing system 1. Referring to this flow chart, the following describes the operation of the radiographic image photographing system 1 when radiographic image data is generated by the radiation image detecting device 6. It is assumed that a plurality of pieces of radiographing order information relating to radiographing have already been inputted by a doctor or receptionist, and the radiographing order information list shown in FIG. 2 is stored in the external storage device of the management server 2.

The following explanation of the flow chart assumes the case wherein one operator uses a plurality of radiation image detecting devices 6 to perform radiographing operations. From the viewpoint of a plurality of radiation image detecting devices 6 being used in one radiographing room 100, the following explanation is applicable to the case wherein a plurality of operators use different radiation image detecting devices 6 in the same radiographing room 100.

The operator such as a doctor or a radiographing technician operates the input operation section of the console 7 to input the information for starting the radiographing operation. Then the control section of the console 7 receives the radiographing order information list stored in the external storage device of the management server 2, and stores the radiographing order information list in the storing section (Step S1). The input screen H1 for inputting the radiographing order information for scheduled radiographing to be conducted in the radiographing room 100, is displayed on the display section (Step S2).

FIG. 7 is an example wherein the input screen H1 for inputting the radiographing order information for scheduled radiographing is displayed on a display section. As shown in FIG. 7, the input screen H1 is provided with the radiographing order information display column h11 for displaying the radiographing order information list stored in the storing section. The left side of the radiographing order information display column h11 is provided with the input button h12 for inputting the information indicating scheduled radiographing in response to each piece of radiographing order information. A DECIDE button h13 and RETURN button h14 are arranged on the lower side of the radiographing order information display column h11.

The operator operates the input operation section by checking the radiographing order information display column h11 and clicks the input button h12 corresponding to the piece of radiographing order information for the radiographing scheduled this time. It is assumed here that the radiographing order information has been clicked, whose radiographing order ID P1 is through [004], [009] and [010]. If there is no problem after that, the DECIDE button h13 is clicked.

Upon receipt of the input from the input operation section, the control section of the console 7 selects the radiographing order information whose radiographing order ID P1 is [001] through [004], [009] and [010] out of the radiographing order information list stored in the storing section (Step S3). A plurality of pieces of the radiographing order information having been selected is sent through the network N to the radiographing operation apparatus 4 arranged on the front room 100a of the radiographing room 100 (Step S4). Upon receipt of radiographing order information from the console 7, the control section 14 of the radiographing operation apparatus 4 stores the radiographing order information for scheduled radiographing in the storing section 21 (Step S5).

Upon completion of transmission of the radiographing order information to the radiographing operation apparatus 4, the radiation image detecting device 6 best suited to the radiographing conditions of the radiographing order information is taken from the storing room 200 by the operator, and is brought into the radiographing room 100. In this embodiment, two radiation image detecting devices 6 (FPD10 and FPD20) having different types of scintillators and sizes are used to perform radiographing operations. In this example, two radiation image detecting devices 6 are used, but radiation image detecting devices 6 of number larger than this can be used in response to the radiographing conditions of the radiographing order information.

The control section of the tag reader 8 constantly checks whether or not the radiation image detecting device 6 has been detected (Step S6). When two radiation image detecting devices 6 have been carried by the operator into the front room 100a of the radiographing room 100, the control section of the tag reader 8 checks the tag 68 of each radiation image detecting device 6 (Step S6: Yes) and reads out the inherent information of the radiation image detecting device 6 stored in the storing section of the tag 68. The inherent information is sent to the radiographing operation apparatus 4 through the cable C2 (Step S7).

The control section 14 of the radiographing operation apparatus 4 receives the inherent information of each radiation image detecting device 6 from the tag reader 8, and stores the inherent information in the storing section 21 (Step S8). The input screen H3 for inputting the radiographing order information for the radiographing that is to be started out of the radiographing order information for scheduled radiographing is displayed on the display section 17, (Step S9).

FIG. 8 is an example wherein the input screen H3 for inputting the radiographing order information for the radiographing that is to be started is displayed on the display section 17. The radiographing order information display column h31 for displaying the radiographing order information stored in the storing section 21, namely, the radiographing order information for scheduled radiographing in the radiographing room 100 is provided at the center of the input screen H3. Otherwise, the structure is the same as that of the input screen H1 and will not be described to avoid duplication.

The operator operates the input operation section by checking the radiographing order information display column h31 and clicks the input button h32 corresponding to the radiographing order information for the radiographing that is to be started. It is assumed that the radiographing order information has been clicked, whose radiographing order ID P1 is through [004]. If there are no problems after that, the DECIDE button h33 is clicked.

Upon receipt of the input from the input operation section 18, the control section 14 of the radiographing operation apparatus 4 selects a plurality of the radiographing order information whose radiographing order ID P1 is [001] through [004], out of the radiographing order information stored in the storing section 21 (Step S10: Order selection device). The input screen H2 for inputting selection of the radiation image detecting device 6 suited for each radiographing order information having been selected is displayed on the display section 17 (Step S11).

FIG. 9 is an example wherein the input screen H2 for inputting selection of the radiation image detecting device 6 is displayed on the display section 17. The radiographing order information display column h21 for displaying the radiographing order information selected in Step S10 is provided at the center of the input screen H2. Further, an inherent information display column h22 is provided below the radiographing order information display column h21, wherein this inherent information display column h22 displays the inherent information of the radiation image detecting device 6 read by the tag reader 8 in Step S7 and stored in the storing section 21 of the radiographing operation apparatus 4. Further, the right side of the radiographing order information display column h21 is provided with the FPD input column h23 for inputting selection of the radiation image detecting device 6 suited to each piece of radiographing order information. The lower right corner of the screen is provided with a DECIDE button h24 and RETURN button h25.

The operator operates the input operation section 18 by checking the inherent information display column h22, and inputs selection of the radiation image detecting device 6 (FPD10 or FPD20) suited to each piece of radiographing order information in the FPD input column h23.

Upon receipt of the input from the input operation section 18, the control section 14 of the radiographing operation apparatus 4 selects the cassette ID of the inherent identification information, for example, as the inherent information of the radiation image detecting device 6, in response to each piece of radiographing order information (Step S12: Inherent information selection device). The radiographing order information is correlated with the cassette ID of the radiation image detecting device 6 (Step S13: Correlation device). This correlation information is stored in the storing section 21. To put it another way, the radiation image detecting device 6 having a cassette ID of FPD10 is assigned to the radiographing order having the radiographing order ID P1 of [001] and [002]. The radiation image detecting device 6 having a cassette ID of FPD20 is assigned to the radiographing order having the radiographing order ID P1 of [003] and [004]. The correlated radiographing order information is sent to each radiation image detecting device 6 through the communication section 19 (Step S14). The flow of FIG. 10 is now complete.

After that, although not illustrated, radiographing operations are performed using the two radiation image detecting devices 6 (FPD10 and FPD20) successively, and radiographic image data based on the correlated radiographing order information is generated. The radiographing order information and the cassette ID related to the generated radiographic image data are sent to the console 7 by wireless communication through the base station 5.

In the console 7, upon receipt of the radiographic image data and radiographing order information, predetermined image processing is performed to the radiographic image data. After that, the radiographic image data and radiographing order information are correlated with each other and are stored. When all the radiographing operations have been completed and transmission to the console has also been completed, the control operation goes back to the radiographing operation apparatus 4. When the END RADIOGRAPHING button H26 has been pressed, the two radiation image detecting devices 6 (FPD10 and FPD20) can be correlated with new radiographing order information. Then the Steps S9 through S14 are repeated. The same radiation image detecting device 6 (FPD10 or FPD20) is used to perform the radiographing operation corresponding to the remaining radiographing order information in the radiographing room 100.

In the manner described above, in constitution of the present embodiment, the tag reader 8 connected with the radiographing operation apparatus 4 is arranged in the front room 100a of the radiographing room 100. The tag 68 of the radiation image detecting device 6 brought into the radiographing room 100 is read out by the tag reader 8, and the inherent information of the radiation image detecting device 6 having been obtained is sent to the radiographing operation apparatus 4. The radiographing order information for the radiographing that is to be started, and the radiation image detecting device 6 suited to this radiographing order information are selected by the radiographing operation apparatus 4, and the radiation image detecting device 6 having been selected is correlated with the radiographing order information.

Thus, when radiographing operations are performed using a plurality of radiation image detecting devices 6, precise correlation can be established between the radiation image detecting device 6 and radiographing order information by the radiographing operation apparatus 4. This arrangement eliminates the possibility of confusing the radiographic image data. Thus, when one operator performs a radiographing operation using a plurality of radiation image detecting devices 6, this arrangement ensures selection of the radiation image detecting device 6 best suited to the radiographing conditions, whereby radiographing operations can be performed. This provides high-quality radiographic image data.

When a plurality of operators uses different radiation image detecting devices 6 to perform radiographing operations in one radiographing room 100, precise correlation can be established between the radiographing order information for scheduled radiographing, and the radiation image detecting device 6 to be used by each operator. This eliminates the possibility of confusion of radiographic image data among different operators.

Even when continuous radiographing operations are performed using the same radiation image detecting device 6, the radiation image detecting device 6 having terminated radiographing can be used for the next radiographing. Accordingly, the next radiographing operation can be started without having to move the radiation image detecting device 6 out of the radiographing room 100 in order to be read out by the tag reader 8.

To be more specific, the inherent information of the radiation image detecting device 6 read out from the tag reader 8 is sent to the radiographing operation apparatus 4 and is stored in the storing section 21. Thus, even when continuous operations are performed using the radiation image detecting device 6, the radiation image detecting device 6 having been used for the radiographing need not be read out again by the tag reader 8. Thus, at the time of continuous radiographing operations, the next radiographing operation can be started without having to move the radiation image detecting device 6 out of the radiographing room 100, whereby a smooth radiographing operation can be conducted.

The storing room 200 for storing the radiation image detecting devices 6 is arranged outside the radiographing room 100, and a plurality of operators are jointly allowed to use the radiation image detecting devices 6. This arrangement ensures improved operation efficiency of the radiation image detecting device 6.

The tag reader 8 preferably detects the moving direction of the radiation image detecting device 6 so that the entry and exit of the radiation image detecting device 6 into and out of the room can be checked. This configuration ensures that, when the radiation image detecting device 6 has exited the radiographing room 100, the inherent information corresponding to the radiation image detecting device 6 is deleted from the display section 17 of the radiographing operation apparatus 4, and only the inherent information corresponding to the radiation image detecting device 6 which can be used can be displayed in real time.

In the above description, the radiographic image data stored in the radiation image detecting device 6 and the radiographing order information are sent to the console 7 from the radiation image detecting device 6 through the base station 5. It is also possible to make such an arrangement, for example, that they are sent to the radiographing operation apparatus 4 instead of the console 7. This arrangement will eliminate the need of sending the radiographing order information from the radiographing operation apparatus 4 to the radiation image detecting device 6, as shown in Step S14 of FIG. 10. To be more specific, in the radiographing operation apparatus 4, the inherent information of the radiation image detecting device 6 and radiographing order information are correlated with each other. If radiographic image data is sent from the radiation image detecting device 6, the radiographic image data and the radiographing order information can be correlated with each other in the radiographing operation apparatus 4, based on the inherent information of the radiation image detecting device 6.

Figure 11:
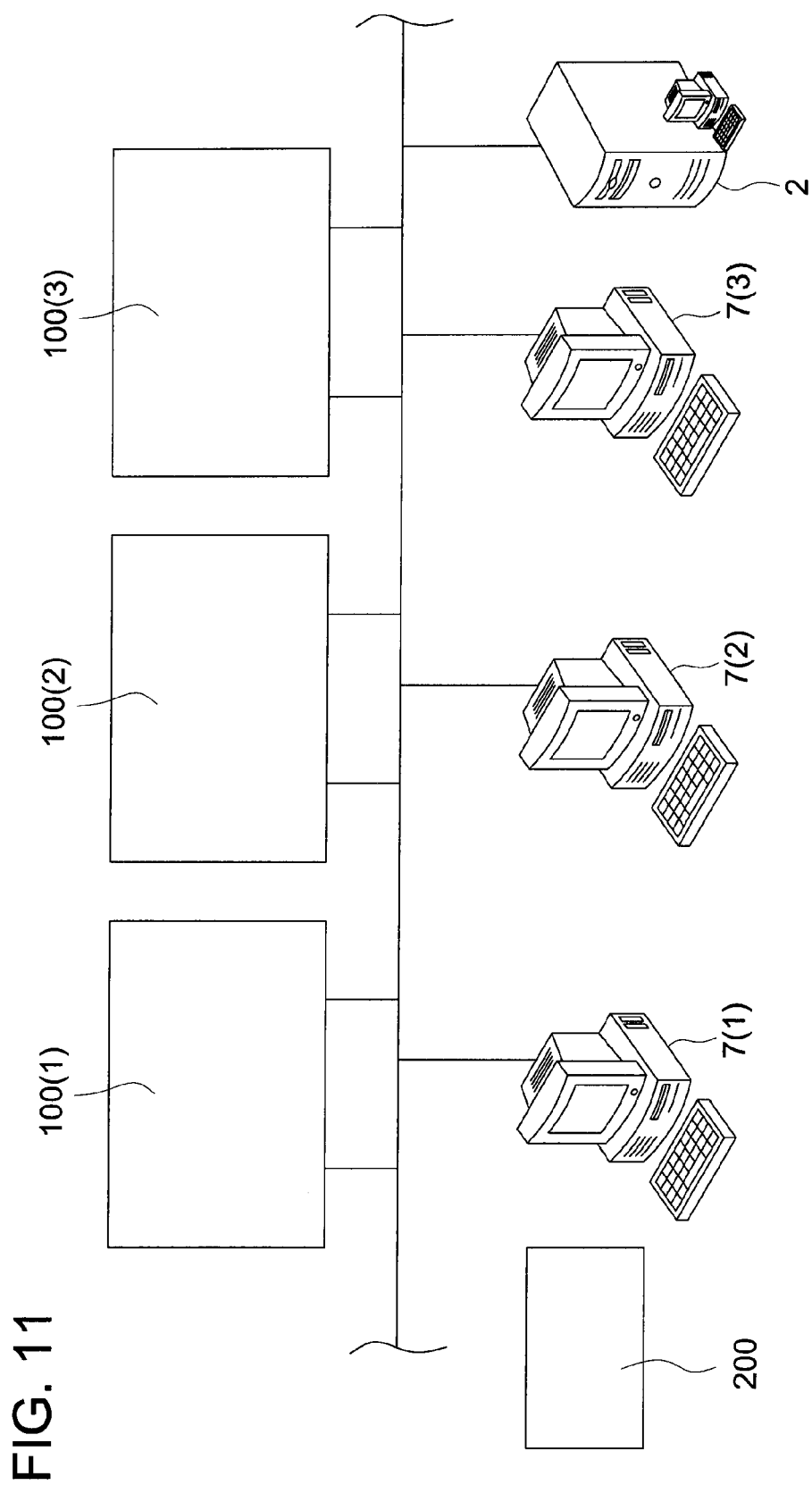
FIG. 11 is a diagram showing the overall structure of the radiographic image photographing system in another embodiment.

FIG. 11 is a diagram showing the overall structure of the radiographic image photographing system 1 in another embodiment of the present invention. The radiographic image photographing system shown in FIG. 11 is connected with a plurality of radiographing rooms 100(1), 100(2) and 100(3) and a plurality of consoles 7(1), 7(2) and 7(3) via the network N. Each of the radiographing rooms 100, each of consoles 7 and each of storing rooms 200 are the same as those shown in FIGS. 1 through 6. Each radiographing room 100 is equipped with a radiographing operation apparatus 4, base station 5 and tag reader 8.

In the embodiment of FIG. 11, the cassette ID of the radiation image detecting device 6 placed in each radiographing room 100 is collected by the radiographing operation apparatus 4, and the cassette ID is sent from the radiographing operation apparatus 4 to the console 7. This makes it possible to clarify, on the console 7, which radiation image detecting device 6 is placed in which radiographing room 100.

Figure 12:
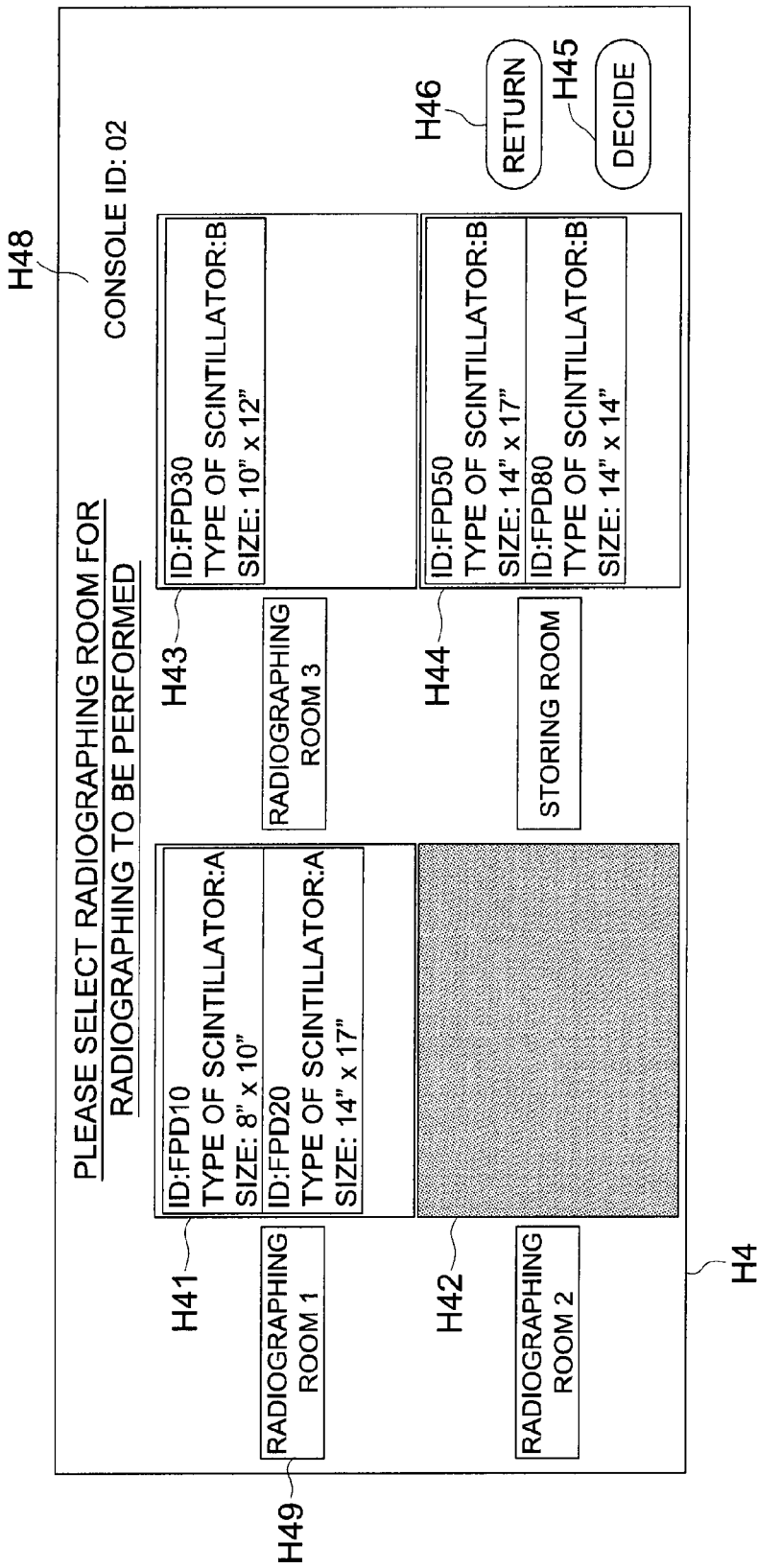
FIG. 12 is an example showing the radiation image detecting devices 6 arranged in the radiographing rooms 100.

FIG. 12 is an example showing, on the display section of the console 7, the radiation image detecting device 6 arranged in each radiographing room 100. In this diagram, in the case of the radiographing room 100 for performing radiographing operations (e.g., radiographing room 1), the console ID of the console displaying the relevant display screen H4 is displayed in the ID display column H48, and the cassette ID of the radiation image detecting device 6 arranged in each room is displayed in the radiographing room display columns H41 through H43 and storing room display column H44. The radiographing room 100 for scheduled radiographing can be selected by clicking the button H49 corresponding to the radiographing rooms 100 (rooms 1 through 3 in this diagram) for scheduled radiographing. After selection, the DECIDE button H45 is pressed, whereby the input screen for inputting the radiographing order information for scheduled radiographing in FIG. 7 appears. After that, the operation is performed according to the diagrams of FIGS. 7 through 9 and the flow chart of FIG. 10.

In the storing room 200, when the radiation image detecting device 6 has been loaded into each slot of the cradle, the battery built in the power source section 67 is charged through the charging terminal 69, and the cassette ID of each radiation image detecting device 6 loaded in each slot is notified to each of the consoles 7 via the network N. This permits display of the scintillator type and size of the radiation image detecting device 6 kept in the storing room.

According to the present embodiment, an operator such as the radiographing technician and doctor wishing to start a new radiographing operation can select the radiographing room 100 wherein a desired radiation image detecting device 6 is placed. This eliminates the need of unwanted motions (movements) to got to the storing room 200. This arrangement is therefore preferred. Further, at the time of completing the radiographing operation, even if the radiation image detecting device 6 is left in the radiographing room 100, the entire system is kept under smooth operating conditions. This reduces the loads on the radiographing technician and others.

What is claimed is:

1. A radiographic imaging system comprising:
   a portable radiation image detecting device which is operable in a plurality of radiographing rooms;
   a checking device which is installed in each of the plurality of radiographing rooms and which checks the portable radiation image detecting device entering into and going out of a radiographing room and reads identification information of the portable radiation image detecting device; and
   a display unit which is installed in each of the plurality of radiographing rooms and which displays a checking result of the checking device,
   wherein the system is configured such that the display unit displays information of the portable radiation image detecting device entering into each radiographing room corresponding to the checking result of the checking device, and the display unit stops displaying the information of the portable radiation image detecting device going out of each radiographing room corresponding to the checking result.

2. The radiographic imaging system of claim 1, comprising a plurality of the portable radiation image detecting devices, wherein the radiographic imaging system checks an ID of each plurality of the portable radiation image detecting devices and individually displays the information together with the ID of each of the portable radiation image detecting devices entering into each radiographing room.

* * * * *